United States Patent
Goldammer et al.

(10) Patent No.: US 8,197,129 B2
(45) Date of Patent: Jun. 12, 2012

(54) METHOD AND APPARATUS FOR DETERMINING COMPONENT PARAMETERS BY MEANS OF THERMOGRAPHY

(75) Inventors: Matthias Goldammer, München (DE); Werner Heinrich, Bärenklau (DE)

(73) Assignee: Siemens Aktiengesellschaft, Munich (DE)

( * ) Notice: Subject to any disclaimer, the term of this patent is extended or adjusted under 35 U.S.C. 154(b) by 574 days.

(21) Appl. No.: 12/310,856

(22) PCT Filed: Sep. 7, 2007

(86) PCT No.: PCT/EP2007/059413
§ 371 (c)(1),
(2), (4) Date: Mar. 10, 2009

(87) PCT Pub. No.: WO2008/031774
PCT Pub. Date: Mar. 20, 2008

(65) Prior Publication Data
US 2009/0201971 A1 Aug. 13, 2009

(30) Foreign Application Priority Data
Sep. 15, 2006 (DE) .......... 10 2006 043 339

(51) Int. Cl.
*G01B 11/06* (2006.01)
*G01B 21/08* (2006.01)
*G01N 25/72* (2006.01)

(52) U.S. Cl. .......... 374/120; 374/5; 374/7; 250/330

(58) Field of Classification Search .......... 374/5, 7, 374/43, 44, 137, 147, 45, 120; 250/330, 250/340, 341, 341.6, 341.8
See application file for complete search history.

(56) References Cited

U.S. PATENT DOCUMENTS

| | | | |
|---|---|---|---|
| 394,646 A | 12/1888 | Hammons | |
| 3,566,669 A * | 3/1971 | Lawrence et al. | 374/5 |
| 4,551,030 A * | 11/1985 | Luukkala et al. | 374/5 |
| 455,760 A | 12/1985 | Busse | |
| 487,811 A | 10/1989 | Thomas et al. | |
| 5,111,046 A * | 5/1992 | Bantel | 250/330 |
| 5,803,606 A * | 9/1998 | Petry et al. | 374/45 |
| 6,367,968 B1 * | 4/2002 | Ringermacher et al. | 374/7 |
| 6,367,969 B1 * | 4/2002 | Ringermacher et al. | 374/7 |
| 6,394,646 B1 * | 5/2002 | Ringermacher et al. | 374/7 |
| 6,516,084 B2 * | 2/2003 | Shepard | 382/141 |

(Continued)

FOREIGN PATENT DOCUMENTS
DE 4203272 A1 8/1993
(Continued)

OTHER PUBLICATIONS
Wu et al., "Lock-in Thermography for Nondestructive Evaluation of Aerospace Structures" ECNDT—Session: Aerospace, Sep. 1998, pp. 1-6, vol. 3, Nr. 9, XP-002462637.

(Continued)

*Primary Examiner* — R. A. Smith

(57) ABSTRACT

A method for determining parameters of a component using thermography, where at least one component is heated by a hot gas, is provided. Also provided is a device for determining component parameters using thermography, including a device for heating at least one component and a temperature sensor for detecting at least one temperature value of the component, wherein the device for heating the component is a hot gas emission device for the emission of a modulated, mostly pulsed, hot gas.

16 Claims, 1 Drawing Sheet

U.S. PATENT DOCUMENTS

| | | | |
|---|---|---|---|
| 6,595,685 B2 * | 7/2003 | Baba et al. | 374/161 |
| 6,812,468 B1 * | 11/2004 | Baumann et al. | 250/341.6 |
| H2127 H * | 10/2005 | Byrd | 374/121 |
| 7,044,634 B2 * | 5/2006 | Sandvoss | 374/5 |
| 7,724,925 B2 * | 5/2010 | Shepard | 382/115 |
| 2002/0172410 A1 | 11/2002 | Shepard | |
| 2004/0225482 A1 * | 11/2004 | Vladimirov et al. | 703/2 |
| 2006/0029121 A1 | 2/2006 | Boehmisch et al. | |

FOREIGN PATENT DOCUMENTS

| | | |
|---|---|---|
| DE | 4343076 A1 | 6/1995 |
| DE | 19720461 A1 | 2/1998 |
| DE | 10103689 A1 | 8/2002 |
| DE | 10118131 C2 | 6/2003 |
| DE | 102007058566 A1 * | 6/2009 |
| EP | 1203199 B1 | 5/2002 |
| EP | 1203224 B1 | 5/2002 |
| WO | WO 00/11450 A2 | 3/2000 |
| WO | WO 00/63642 A1 | 10/2000 |
| WO | WO 01/07867 A1 | 2/2001 |
| WO | WO 01/41421 A2 | 6/2001 |
| WO | WO 2004/031726 A2 | 4/2004 |
| WO | WO 2004/048775 A2 | 6/2004 |
| WO | WO 2006/037359 A1 | 4/2006 |

OTHER PUBLICATIONS

Maldague et al., "Pulse phase infrared thermography", J. Appl. Phys., Mar. 1, 1996, pp. 2694-2698, vol. 79, No. 5.

* cited by examiner

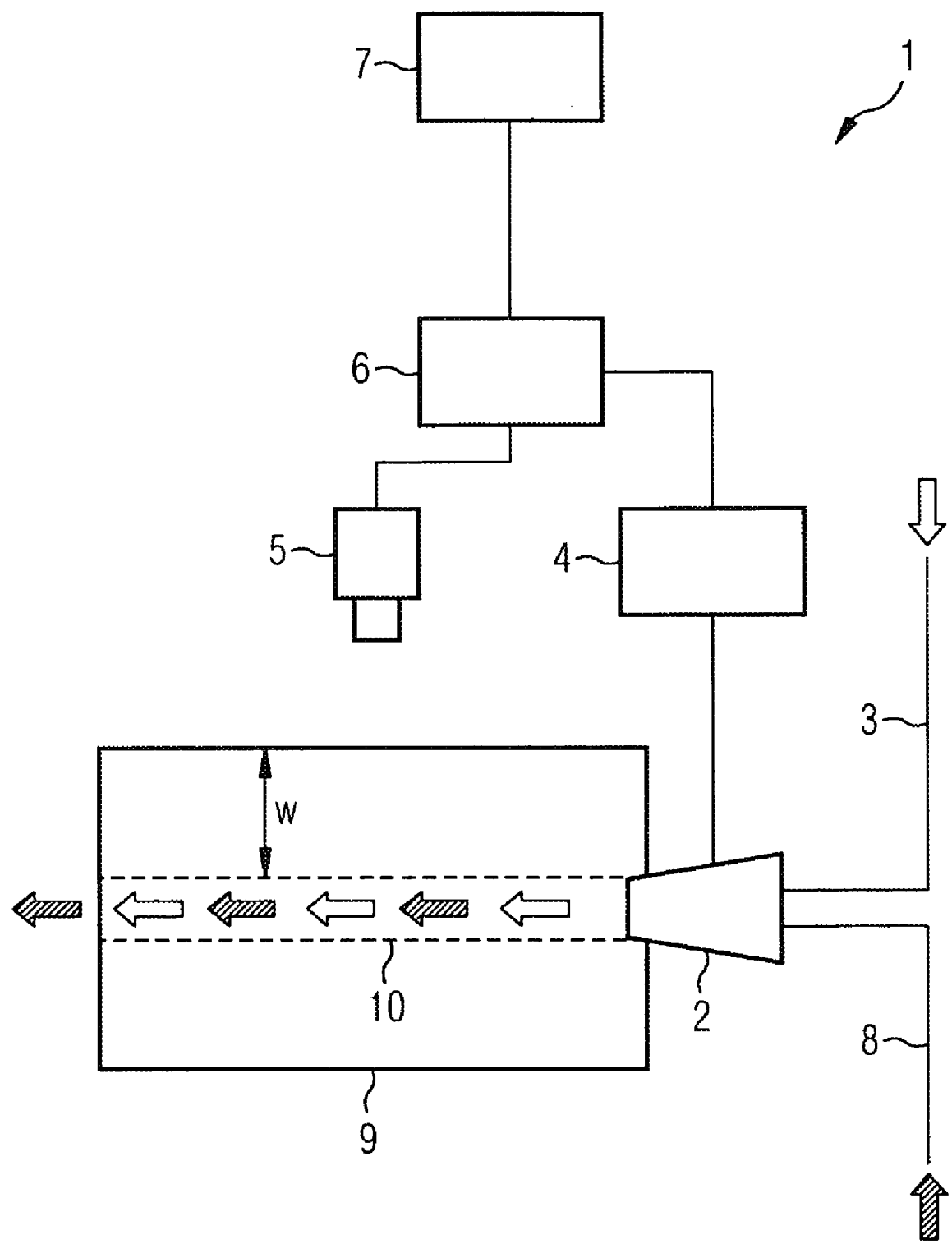

METHOD AND APPARATUS FOR DETERMINING COMPONENT PARAMETERS BY MEANS OF THERMOGRAPHY

CROSS REFERENCE TO RELATED APPLICATIONS

This application is the US National Stage of International Application No. PCT/EP2007/059413, filed Sep. 7, 2007 and claims the benefit thereof. The International Application claims the benefits of German application No. 10 2006 043 339.4 DE filed Sep. 15, 2006, both of the applications are incorporated by reference herein in their entirety.

FIELD OF INVENTION

The invention relates to a method and a device for determining component parameters by means of thermography.

BACKGROUND OF INVENTION

Thermography has recently established itself alongside other methods for characterizing components such as, for example, ultrasound, magnetic-field and eddy-current methods, since, in contrast to the other methods, it works contactlessly and through imaging and can thereby achieve an increased measurement speed and an increased resolution and can be automated more easily.

A variety of approaches exist for determining quantitative parameters such as, for example, the geometry of a component or its thermal properties by means of thermography. Common to all thermographic measurement methods is their use of infrared radiation, which is radiated from the surface of a heated component in order to record a temporal progression of the surface temperature. A thermal imaging camera is frequently used for capturing the infrared radiation, in order to record a temporal progression of a planar thermal image.

To determine material parameters, frequently not only is the intrinsic heat of the component used, but, in addition, heat is introduced into the component so as selectively to induce a thermal flux. To heat the component, hitherto known methods include, among others, application of en electric current, irradiation with microwaves, use of chemical processes and use of radiation (lasers, halogen lamps, flash-lamps). Of these methods, the use of flash-lamps, in which light pulses are emitted by the flash-lamps which heat the component surface, is particularly widespread. The thermal flux generated in this manner is directed from the surface into the component. By analyzing the surface temperature, a parameter such as a wall thickness can be determined: the surface temperature decreases as long as the heat can flow away into the interior and reaches a constant level once the thermal front has reached the back of the component and the heat has consequently spread evenly throughout the component. The time needed to produce the thermal equilibrium and thus the temperature on the measured component surface is a measure of the component thickness (wall thickness).

Several methods for determining a wall thickness by means of flash thermography are known. In one method, the measured temperature signal is compared with a reference signal which is either measured, as disclosed in EP 1173724, or is calculated, as disclosed in EP 1203224. Alternatively, the time-dependent temperature signal can be transformed into the frequency domain, as known for example from EP 1203199 or Maldaque X. P., Marinetti S., "Pulse Phase Infrared Thermography"; J. Appl. Phys., 79(5) (1996), pages 2694-2698. WO 2001/41421 discloses a method for calculating the derivation of data recorded with an infrared detector in order to determine the wall thickness by means of the position of an extreme value in the derivation of the time-temperature signal.

However, use of a pulsed excitation, as occurs in flash-lamps, restricts the maximum measurable thickness: if the temperature difference on the surface falls below the noise level of the detector, the transient surface temperature can no longer be evaluated. If the object to be measured permits higher surface temperatures, multiple pulses can increase the heat supply, or the excitation period can be increased. As an alternative to this, a continuously modulated heat source can be used with suitable evaluation methods which, together with lock-in detection methods, can reduce the noise depending on the measurement period, as described, for example, in U.S. Pat. No. 4,878,116 and DE 4203272. WO 2000/11450 discloses a use of multiple frequencies at one time.

DE 4343076 C2 discloses a device for the thermal testing of a surface of, in particular, a moving object by means of thermography with optical excitation.

WO 2006/037359 A1 discloses a method for determining material parameters of an object from data of a temperature-versus-time plot.

SUMMARY OF INVENTION

The object of the present invention is therefore to provide a reliable and accurate facility for determining parameters also of larger dimensions by means of thermography.

This object is achieved in a method according to and in a device according to the independent claims. Advantageous embodiments can be found, singly or in combination, in particular, in the subclaims.

The method is characterized in that at least one component is heated by means of a hot gas. Through the use of hot gas, high heat generation in the component is possible. In addition, where hot gas is used, the heat generation can be controlled particularly well, since the quantity of gas supplied, the conduction of the gas and the temperature of the hot gas can all be adjusted independently.

It is particularly advantageous if at least one component is heated by generally modulated hot gas, in particular by one or more pulses of hot gas. By this means, evaluation methods matched to the modulated or pulsed thermal excitation can be used e.g. for flash-lamp or laser excitation. The pulses can be changed in the course of measurement, e.g. in their pulse duration or the duration of the interval between the pulses. The pulses can also be superimposed over a continuous gas supply. Furthermore, various pulse sequences, including of different frequency and amplitude, can be superimposed.

The pulsed gas supply has, in particular, the advantage that for one or more frequencies which are present in the pulse sequence, a phase angle of a between the pulses of the hot gas and the modulation of a temperature measured on the surface of the component can be determined, as a result of which a wall thickness of the component or thermal material parameters can usefully be determined. This can occur particularly advantageously if a monofrequency excitation is used, as in this way from the phase angle of the component or object the wall thickness can be determined comparatively easily if the thermal conductivity is known and the thermal conductivity can be determined comparatively easily if the wall thickness is known. Here, the fact is exploited that the phase angle correlates with the duration of heat pulses in the component.

A lock-in method is preferably used for detecting signal values as this permits reliable phase determination. However, lock-in methods are susceptible to slow drift, in the case of thermography therefore when a slow temperature shift is superimposed on the desired periodic signal. This drift causes an additional signal which is superimposed on the useful signal and leads to a phase error which turns out to be all the greater, the weaker the useful signal relative to the additional signal is. To reduce or even to eliminate the evaluation error generated by the temperature drift, two methods which are applied to the raw data prior to calculation of the wall thickness are especially suitable:

(a) A lateral running average of the measurement data is calculated and used. If an averaging length is used which corresponds to an integral multiple of the period length, the averaged data contains no useful signal at all, but consists exclusively of temperature drift. If the averaged data is subtracted from the original signal prior to the lock-in calculation, the drift signal is largely suppressed. The first and last half period can each be cut off before the lock-in calculation. Instead of a running average value which corresponds to a convolution with a square convolution kernel, any other symmetrical convolution kernel with the length of an integral multiple of the period length can be used. As a result, it is additionally possible in the same computational step to suppress further unwanted frequencies prior to the lock-in calculation.

(b) The raw data is approximated by a lower-order (e.g. linear or quadratic) polynom fit, by means of which the useful signal is suppressed in the resulting curve. The polynom determined is deducted from the raw data before the lock-in calculation in order to remove the drift. The calculation is preferably carried out for each pixel. Compared with method (a), drift suppression is lower, but the computational outlay is reduced. In order to improve accuracy where there are only few measurement cycles, artificial data can be introduced and fed into the lock-in calculation, e.g. a sinusoidal function.

In order to improve the accuracy of the phase and amplitude values obtained from the lock-in calculation, it is possible to carry out a lateral averaging over the image. In contrast to the averaging methods normally used, here both a phase image and an amplitude image are available for image processing. Where the individual pixel values are used as complex numbers, effective averaging of the phase images taking the amplitude into account is possible. To do this, the phase and amplitude image is combined into a new image consisting of complex-value pixels, which are then subjected to suitable averaging methods, such as e.g. a two-dimensional running average value. The newly obtained complex-value image is then converted back again into a phase and amplitude image.

The two methods under (a) and (b) are not restricted to hot-gas thermography, but represent an independent invention for any lock-in calculation in which a slow signal change is superimposed over a periodic signal.

The determination of the wall thickness from the phase angle by means of a—calculated or measured—calibration curve is particularly advantageous in the case of complex components.

To extend the area of determination, it is particularly advantageous if the modulation of the temperature of the component is measured for various oscillation modes, in particular for a fundamental oscillation, which corresponds to the pulse pattern of the hot-gas thermal excitation, and for a second harmonic.

To increase the measurement accuracy, it is advantageous if the at least one component is cooled in periods between pulses of the supplied hot-gas, in particular by pulses of cool gas. The component is thus cooled between the pulses of hot gas by pulses of cool gas. Such a cooling also has the advantage that a temperature change produced by hot gas (during heating) and by cool gas (during cooling) is similar, since the component is treated by gas both times. The pulses of hot gas do not have to exhibit the same duration or form, nor do they have to follow one another directly.

It is also favorable if, furthermore, an amplitude of a temperature modulation of the frequencies for which the phase angle is captured is determined in the component as in this way a measurement accuracy of the measured parameters of the component can be determined from the phase and amplitude determined and from a noise in a recorded thermal image.

The method can be applied particularly favorably if the hot gas is introduced into an interior of a hollow component, in particular into a turbine blade.

The object is also achieved in a device for determining component parameters by means of thermography, comprising a heating means for heating at least one component and a temperature sensor for recording at least one temperature value of the component, the heating means for heating the component being a hot-gas emission device for the emission of modulated, especially pulsed, hot gas.

To capture a phase angle between pulses of a thermal excitation and a temperature of the surface of the component, the device favorably has a lock-in circuit.

For the fast and accurate detection of measured values, the temperature sensor is preferably a thermal imaging or infrared camera. It can then be favorable if the evaluation is carried out pixel by pixel. It can also be favorable if a display unit displays a representation on the basis of a superimposition of multiple thermal images which have been recorded from various angles, in particular a wall-thickness image of the component.

It can be also favorable if the device also has a cool-gas-supplying means for supplying cool gas to an area heated by the hot gas.

The invention will be explained in detail below purely schematically with the aid of a selected exemplary embodiment which is not intended to restrict the invention.

BRIEF DESCRIPTION OF THE DRAWINGS

FIG. 1 shows a sketch of an exemplary embodiment for the thermographic measurement of a workpiece.

DETAILED DESCRIPTION OF INVENTION

FIG. 1 shows a device 1 for determining component parameters by means of thermography. The device 1 has a heating means in the form of a hot-gas emission device 2 for the emission of pulsed hot gas, which device is connected to a hot-gas supply line 3. The hot-gas emission device 2 is connected furthermore to a control device 4 which emits control signals to the hot-gas emission device 2 in order to control the pulses, e.g. a pulse frequency, a pulse height and/or a pulse duration.

The device 1 also has a temperature sensor in the form of a thermal imaging camera 5. The thermal imaging camera 5 and the control device 4 are connected to a lock-in circuit 6 for capturing a phase angle between pulses of a thermal excitation, here derived from the control pulses of the control device 4, and a temperature measured by the thermal imaging camera 5. The results of the lock-in circuit 6 are executed by an evaluation and display unit 7 in order to be converted there into an image which can be evaluated for a user and which shows the component parameters to be determined.

To increase the measurement accuracy, the hot-gas emission device 2 is connected furthermore to a cool-gas line 8. By switching the hot-gas emission device 2 appropriately, by means of the control device 4 hot gas (supplied through the hot-gas supply line 3, as indicated by the white arrow) or cool gas (supplied through the cool-gas supply line 3, as indicated by the black arrow) can optionally be emitted from the hot-gas emission device (as indicated by the alternating sequence of white and black arrows).

In this FIG. 1, the application of the device 1 for measuring a wall thickness w of a gas-turbine blade 9 as a component will now be described in greater detail. The gas-turbine blade 9 has type-dependently at least one cooling channel 10 by which the gas-turbine blade 9 is cooled during operation.

For quality control purposes, the wall thickness w between the cooling channel 10 and the external surface of the gas-turbine blade 9 has hitherto been checked by means of ultrasound methods or by flash-lamp thermography, for example. Unfavorably, flash-lamp thermography can no longer reliably be applied to gas-turbine blades 9 thicker than 4-5 millimeters for the aforementioned reasons, as the remaining temperature difference to be measured is comparable to the noise of the thermal imaging camera 5.

In the application shown here, on the other hand, hot gas is introduced into the existing cooling channel 10 of the gas-turbine blade 9. As a result, the gas-turbine blade 9 is heated from the inside, and some of the heat flows to the surface of the gas-turbine blade 9, where it is recorded in a defined surface section by the thermal imaging camera 5. This is particularly advantageous if no further cooling channels have been drilled through the surface.

In the embodiment shown:
the blade 9 is fastened in an air-tight holder (not shown);
a thermal imaging camera captures the surface temperature of the blade 9 in an area;
at the same time, compressed air is conducted through the cooling channel 10 of the blade 9, and this is done alternating between hot air which has been heated to approx. 80° C. and compressed air at ambient temperature in 10 to 20 cycles of 0.5 Hz to 2 Hz. The load cycle from hot to cold air typically fluctuates between 10% and 50%;
for each pixel of the resulting infrared video produced, a lock-in calculation is carried out which yields a phase and amplitude value which is converted into a wall-thickness value and displayed; and
the measurement is carried out from 4 to 5 different angles in order to cover the whole surface of the vane of the gas-turbine blade 9.

A thermography method in which hot gas is introduced into an interior of a hollow component, in particular into a turbine blade, exhibits a series of advantages and improvements compared with other thermography methods, in particular compared with flash-lamp and laser thermography:

Turbine blades which are designed to be cooled by air are ideal for excitation by means of hot air as all the critical points to be investigated are also reached automatically by the hot air.

Since the heating is achieved by thermal convection, the quantity of heat transferred to the component does not depend on optical properties of the component, as for example in the case of flashlight or laser excitation.

The lock-in detection effectively suppresses noise originating from the IR camera so that the signal quality can easily be improved by measuring additional cycles so that a required accuracy can be adjusted by the measurement time.

The measurement is designed for a transmission configuration. A heat wave therefore needs to pass through the component only once, which results in a better signal in comparison to a unilateral design, as for example in the case of flashlight or laser excitation.

Hitherto, in known pulsed thermography methods, the component temperature increased with each shot, as a result of which the signal strength decreased. The component temperature can be limited in the method shown by supplying cool air between the hot-gas pulses, such that the signal strength can be held at a defined level. In addition, between reconfiguration of the measurement device in order to record the component from a new angle, cool air can be supplied in order to cool the component to the same initial temperature for each recorded angle. In this way, multiple angles can be measured rapidly without additional equipment.

Since not only the phase but also the amplitude is captured, the accuracy of the wall-thickness calculation can be determined. Through determination of the accuracy, the method can be further improved as now only areas of the component which reach a predetermined accuracy level are used for wall-thickness determination. For example, in the case of pixel-by-pixel calculation, those pixels from a recorded image which do not reach the predetermined accuracy level can be faded out. A user can thus rely on the predetermined accuracy level.

To calculate the wall thickness w from the respectively measured phase and amplitude, a calibration curve is used in this embodiment, which curve is produced on the basis of a reference component, e.g. a pipe having a changing, known wall-thickness. Alternatively, the calibration curve can be established by means of an analytical model, e.g. by means of a finite-elements method. It is particularly advantageous here if the calibration curve is determined for various oscillation modes, e.g. the fundamental oscillation and the second harmonic. The use of higher oscillation modes reveals the advantage that the reliably measurable wall-thickness range is extended down to smaller values and also that details of the recorded image can be displayed more finely where a recording using lower modes, e.g. the fundamental oscillation, would be more blurred due to the lateral thermal expansion.

Where various oscillation modes are used, the wall-thickness calculation can be carried out in three fundamental steps:

Determination of the phase and amplitude of the excitation frequency and of harmonics for each pixel.

Calculation of the thickness and of the accuracy value for each pixel using the analytical calibration curve. Accuracy values below a predetermined accuracy-value threshold are faded out.

The wall-thickness values of the different oscillation modes are plotted into a single wall-thickness image map and presented to the user.

The present embodiment is not of course restricted to the exemplary embodiment described above. For example, other hollow components can also be used. Also, non-hollow components can be used in which hot gas is radiated onto the surface from the outside.

The invention claimed is:
1. A method for determining parameters of a component using thermography, comprising:
heating a component with a hot gas;
determining a measurement accuracy of a parameter of the component from a determined phase and an amplitude of a measured temperature and from a noise in a recorded thermal image;
determining a phase angle between the plurality of pulses of the hot gas and a temperature which is measured on a surface of the component, wherein the component is heated by a plurality of pulses of the hot gas.

2. The method as claimed in claim 1, further comprising cooling the component by a plurality of pulses of a cool gas between the plurality of pulses of the hot gas.

3. The method as claimed in claim 1, further comprising determining a wall thickness of the component from the phase angle wherein the wall thickness is one of the parameters being determined.

4. The method as claimed in claim 3, wherein the wall thickness is determined from the phase angle using a calibration curve.

5. The method as claimed in claim 1, wherein the hot gas is introduced into an interior of the hollow component.

6. The method as claimed in claim 5, wherein the hollow component is a turbine blade.

7. The method as claimed in claim 1, wherein the non-hollow component is used in which the hot gas is radiated onto the surface from an outside of the component.

8. A method for determining parameters of a component using thermography, comprising:
   heating a component with a hot gas;
   determining a phase angle between a plurality of pulses of the hot gas and a temperature which is measured on a surface of the component;
   determining a measurement accuracy of a parameter of the component from a determined phase and an amplitude of a measured temperature and from a noise in a recorded thermal image; and
   determining a wall thickness of the component from the phase angle,
   wherein the wall thickness is determined from the phase angle using a calibration curve, and
   wherein the component is heated by the plurality of pulses of the hot gas.

9. The method as claimed in claim 8, wherein the hot gas is introduced into an interior of the hollow component.

10. The method as claimed in claim 9, wherein the component is a turbine blade.

11. The method as claimed in claim 8, wherein the non-hollow component is used in which the hot gas is radiated onto the surface from the outside of the component.

12. A device for determining a plurality of component parameters using thermography, comprising:
    a device for heating a component; and
    a temperature sensor for recording at least one of a plurality of temperature values of the component,
    a measurement accuracy of a parameter of the component determined from a determined phase and an amplitude of a measured temperature and from a noise in a recorded thermal image, and
    wherein the device for heating the component is a hot-gas emission device which emits a modulated and mostly pulsed hot gas.

13. The device as claimed in claim 12, further comprising, a lock-in circuit which captures a phase angle between a plurality of pulses of a thermal excitation and a temperature of a surface of the component.

14. The device as claimed in claim 12, wherein a wall thickness of the component is determined from the phase angle.

15. The device as claimed in claim 12, wherein the temperature sensor is a thermal imaging camera.

16. The device as claimed in claim 12, further comprising a cool gas supplying device to supply cool gas to an area heated by the hot gas.

* * * * *